United States Patent [19]

Mikkelsen

[11] Plant 5,160

[45] Dec. 20, 1983

[54] KALANCHOE PLANT NAMED CINNABAR

[75] Inventor: James C. Mikkelsen, Ashtabula, Ohio

[73] Assignee: Mikkelsens, Inc., Ashtabula, Ohio

[21] Appl. No.: 418,488

[22] Filed: Sep. 15, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A kalanchoe named Cinnabar having deep orange-red florets in a well formed inflorescence carried on a very vigorous stem having close internodes with medium size, nearly round leaves. The self-branching habit is sufficiently compact for 10 cm. pots yet vigorous enough for larger specimens in 15 cm. pots.

1 Drawing Figure

The present invention relates to a new and distinctive cultivar of kalanchoe plant, botanically known as kalanchoe, and referred to by the cultivar name Cinnabar. Cinnabar was developed by me through controlled breeding by crossing seedling 77-717-55 (seed parent)×seedling 76-453-1 (pollen parent). Asexual reproduction by stem cuttings has shown that the unique features of this new kalanchoe are stabilized and are reproduced true to type in successive propagations.

The following characteristics distinguish the new kalanchoe from both its parent cultivars and other cultivated kalanchoes of this type known and used in the floriculture industry:

1. In comparison to Mercur, disclosed in pending application Ser. No. 439,645 of Heinz Sommer, the flower color of Cinnabar is orange-red, the foliage is more rounded, flower size and inflorescence are larger, and the stems are much heavier.

2. In comparison to Nugget, disclosed in U.S. Plant Pat. No. 4,207, the flower color of Cinnabar is deeper, the foliage broader, and the plant is more vigorous.

3. In comparison to Regulus, disclosed in U.S. Plant Pat. No. 4,817, the flower color of Cinnabar is more red, the stems are heavier, and flowering is nearly two weeks earlier.

4. In comparison to Sirius, disclosed in U.S. Plant Pat. No. 4,103, the flower color of Cinnabar is more red, the plant vigor is greater, and self-branching is more pronounced.

5. The new cultivar is extremely vigorous so that very small starter plants can be used for 10 cm. pot production by putting into short day treatment immediately at potting.

6. The heavy vigorous stems are supporting a large, compact cyme when in full bloom.

7. Individual florets in the inflorescence are large, with the white stigma being quite visible.

8. Flower color is orange-red in low light, low temperature environments, becoming more orange under summer conditions.

9. Inflorescence is quite resistant to botrytis petal blight. Foliage is quite resistant to powdery mildew.

10. In high light and temperature regimes, several applications of growth regulator are needed to help control height and maintain good plant to pot size symmetry.

The accompanying colored photograph taken March, 1982 illustrates in perspective view the overall appearance of Cinnabar grown in 10 cm. plastic pot, and showing the colors as true as it is reasonably possible to obtain in a colored reproduction of this type.

The following is a detailed description of Cinnabar based on plants produced under commercial practices in greenhouses at Mikkelsens Inc., Ashtabula, Ohio. Color references are made to The Royal Horticultural Society Colour Chart except where general terms of ordinary dictionary significance are used.

Parentage: A controlled cross of my seedling 77-717-55 as the seed parent with seedling 76-453-1 as the pollen parent.

Propagation:

(A) *Type cutting.*—Tip or shoot cutting 2 cm. long.

(B) *Time to root.*—10 days at 21° C. summer, 15 days at 21° C. winter.

(C) *Rooting habit.*—Abundant, fibrous, dendritic.

Plant Description:

(A) *Form.* Upright, vigorous, compact, succulent.

(B) *Habit of growth.*—Growth rate and vigor are above average; internodes are somewhat close before flower initiation, and self-branching is uniform the full length of stem.

(C) *Foliage.*—Dark Yellow green, simple, opposite symmetrical. (1) Size: When grown at close production spacing in 10 cm. pots, the leaves are generally 8–9 cm. in diameter. (2) Shape: Orbicular, apex rounded, base obtuse toward rounded. (3) Texture: Glabrous, coriaceous, succulent. (4) Margin: Sinuate. (5) Color: Young foliage top side, yellow green 147A; under side yellow green 147B; mature foliage top side, between yellow green 146A–147A; under side, yellow green 147B.

Flowering description:

(A) *Flowering habits.*—Inflorescence of each peduncle is formed by dichotomous branching, starting with opening of terminal flower of main axis followed by terminal flowers of side branches of each inflorescence. Opening of secondary buds will continue for two months or more. Individual flowers will take 2–3 weeks to mature.

(B) *Natural flowering season.*—Late December thru early January. Flowering time under controlled day length at 20° C. night temperature in summer is 9 weeks; in winter, 13 weeks. Flower development time is directly proportional to the amount of light energy available.

(C) *Flower buds.*—Symmetrically round oblong, up to 7–8 mm. long before opening, to tubular as flower petals mature, sheathed with four green sepals; corolla at maturity up to 15 mm. to flattened petals.

(D) *Flowers borne.*—Compound dichasial cyme on strong peduncles. Floret pedicels generally 5–6 mm. long.

(E) *Quantity of flowers.*—Highly floriferous, with 50 or more florets in flower at one time in each segment of cyme, and additional buds continuing to flower.

(F) *Petals.*—(1) Shape: Nearly round, apex cuspidate. (2) Color top side when opening, greyed orange 169A, fading to orange-red 34B; under side orange-red 33B. (3) Number of petals: Four in each corolla, 6–7 mm. in diameter; total flower diameter up to 18 mm.

(G) *Reproductive organs.*—(1) Stamens: Two sets of four each (a) Anther shape: Flat, color yellow. (b) Filament color: Light green to nearly translucent. (c) Pollen color: Light yellow. (2) Pistils (a) Stigma shape: Flat, irregular, color white. (b) Style color: Light green. (c) Ovaries: 4, celled, size 5–6 mm. when mature, color green.

Disease resistance: Inflorescence resistant to botrytis petal blight and foliage resistant to powdery mildew.

I claim:

1. A new and distinct cultivar of kalanchoe plant known by the cultivar name Cinnabar, as described and illustrated, and particularly characterized by deep orange-red florets; floriferous flowering habit; strong, vigorous stems and vigorous growth habit with close internodes; medium size, nearly round foliage, and excellent self-branching.

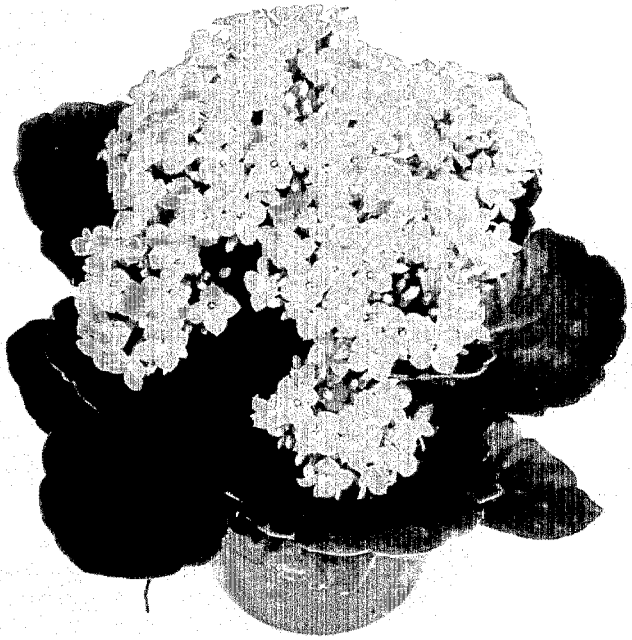

* * * * *